United States Patent [19]

Umezawa et al.

[11] 4,202,824
[45] May 13, 1980

[54] PHYSIOLOGICALLY ACTIVE DERIVATIVES OF ESTERASTIN

[75] Inventors: Hamao Umezawa, Tokyo; Takaaki Aoyagi, Fujisawa; Tomio Takeuchi, Tokyo, all of Japan

[73] Assignee: Zaidan Hojin Biseibutsu Kagaku Kenkyu Kai, Tokyo, Japan

[21] Appl. No.: 33,359

[22] Filed: Apr. 26, 1979

[30] Foreign Application Priority Data

May 25, 1978 [JP] Japan .................................. 53-61725
May 25, 1978 [JP] Japan .................................. 53-61726

[51] Int. Cl.$^2$ ............................................ C07D 305/12
[52] U.S. Cl. ................................ 260/343.9; 435/123; 435/886
[58] Field of Search ...................................... 260/343.9

[56] References Cited

PUBLICATIONS

Umezawa et al., The Journal of Antibiotics 31, No. 6, 639–641 (Jun. 1978).
Kondo et al., The Journal of Antibiotics 31, No. 8, 797–800 (Aug. 1978).

*Primary Examiner*—Natalie Trousof
*Assistant Examiner*—Jane T. Fan
*Attorney, Agent, or Firm*—Richard R. Lloyd

[57] ABSTRACT

Three, new physiologically active derivatives of esterastin are now provided, which inhibit the activity of esterase similarly to the parent esterastin and further exhibit a higher inhibiting activity against cholesterol esterase than the parent esterastin. These three new derivatives are tetrahydroesterastin which is produced by catalytic hydrogenation of esterastin; 3,5-dihydroxy-2-hexylhexadeca-7,10-dienoic 1,3-lactone which is produced by alkaline hydrolysis of esterastin; and 3,5-di-hydroxy-2-hexylhexadecanoic 1,3-lactone which is produced either by alkaline hydrolysis of said tetrahydroesterastin or by catalytic hydrogenation of the product of the alkaline hydrolysis of esterastin.

4 Claims, No Drawings

PHYSIOLOGICALLY ACTIVE DERIVATIVES OF ESTERASTIN

SUMMARY OF THE INVENTION

This invention relates to three, new physiologically active substances which inhibit the enzymatic activity of esterase and which are now named tetrahydroesterastin, 3,5-hydroxy-2-hexylhexadeca-7,10-dienoic 1,3-lactone and 3,5-di-hydroxy-2-hexylhexadecanoic 1,3-lactone, respectively. The latter two compounds may be deemed as a β-lactone derivative of a δ-hydroxymycolic acid. This invention also relates to respective processes for the production of these three new substances by chemically treating esterastin as the starting material. This invention further relates to an immunosuppressive composition for reducing the immune response in living animals which comprises at least one of the three, new physiologically active substances mentioned above as the active ingredient. These new physiologically active substances of this invention are able to inhibit the enzymatic activity of a much larger number of enzymes than are inhibited by esterastin.

BACKGROUND OF THE INVENTION

Esterastin is a known substance which has an esterase-inhibiting activity and which is recovered from the culture as obtained by cultivating a microorganism, *Streptomyces lavendulae* MD4-C1 (identified as FERM-P 3723 or ATCC. 31336). This microorganism was isolated from a soil sample collected in the ground of Biseibutsu Kagaku Kenkyu-sho in Shinagawa-ku, Tokyo, Japan. The production and the nature of esterastin is described, for example, in the "Journal of Antibotics" Vol. 31 No. 6 pages 639–641, U.S. patent application Ser. No. 873,350 and French patent application No. 78-04174. Esterastin is active to reduce the number of the cells forming humoral antibody and also to suppress the cell-mediated immunity. Esterastin is of a very low toxicity and may be used safely as a drug to chemotherapeutically treat diseases and disorders caused by the immune reactions such as contact allergic dermatitis, systemic lupus erythematosus,, autoimmune hemolytic anemia, periarteritis nodosa, myasthenia gravis, arthritis, rheumatism and multiple sclerosis. Furthermore, esterastin may be useful as an immunosuppressive drug in the surgical operations of transplantation of an internal organ such as heart, kidney and muscle. Esterastin is also expected to be useful as an anti-inflammatory agent because it inhibits the inflammation caused by carrageenin.

Esterastin has the following chemical structure

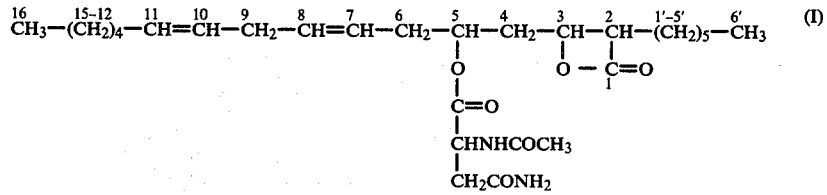

We, the present inventors, have made further research on esterastin and have now found that esterastin is catalytically reduced with hydrogen in the presence of a known hydrogenation catalyst such as platinum oxide or palladium to produce its tetrahydro derivative of the formula

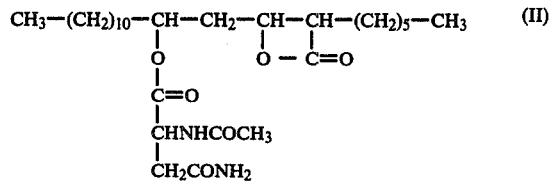

and that this tetrahydro derivative, now named tetrahydroesterastin is active to inhibit the action of esterase similarly to esterastin but exhibits a wider activity in that it inhibits a much larger number of enzymes than can be inhibited by esterastin.

Furthermore, we have now found that when esterastin is hydrolyzed under weakly alkaline conditions, for example, using 0.01 N aqueous solution of sodium hydroxide, there is produced one other esterase-inhibiting substance which is confirmed to be a new compound of the formula

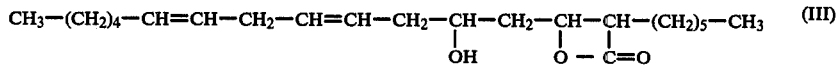

and which is now designated 3,5-di-hydroxy-2-hexylhexadeca-7,10-dienoic 1,3-lactone. Moreover, we have found that when tetrahydroesterastin is hydrolyzed under weakly alkaline conditions, for example, using 0.01 N aqueous solution of sodium hydroxide, there is formed another esterase-inhibiting substance which is confirmed to be a new compound of the formula

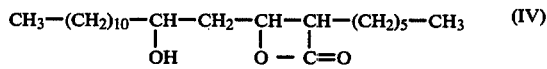

and which is denominated 3,5-di-hydroxy-2-hexylhexadecanoic 1,3-lactone. It is also found that the latter compound may be produced also by catalytically hydrogenating the aforesaid 3,5-di-hydroxy-2-hexylhexadeca-7,10-dienoic 1,3-lactone in the presence of a known hydrogenation catalyst such as platinum oxide or palladium. These two, new compounds are also active to inhibit the action of esterase similarly to esterastin but have wider activity in that they inhibit a much larger number of enzymes than are inhibited by esterastin.

DETAILED DESCRIPTION OF THE INVENTION

According to a generic aspect of this invention, therefore, there is provided the compound of the formula

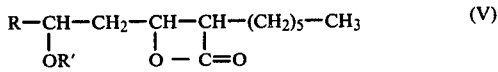

wherein R denotes a group of the formula $CH_3-(CH_2)_4-CH=CH-CH_2-CH=CH-CH_2-$ or a group of the formula $CH_3-(CH_2)_{10}-$ and R' denotes a hydrogen atom or a group of the formula

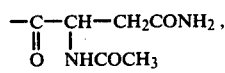

provided that when R' is the group

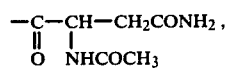

R is the group $CH_3-(CH_2)_{10}-$.

The new compound (V) of this invention includes tetrahydroesterastin, 3,5-di-hydroxy-2-hexylhexadeca-7,10-dienoic 1,3-lactone and 3,5-di-hydroxy-2-hexylhexadecanoic 1,3-lactone as the specific examples thereof.

(1) Tetrahydroesterastin is obtained as a colorless powdery substance of the following properties:

Thus, it shows a melting point of 102.5°–104° C. and a molecular weight of 510 as determined by mass spectrometry. It gives an elemental analysis: C 65.84%, H 9.71%, N 4.93%, O 18.12% and is coincident with a molecular formula $C_{28}H_{50}N_2O_6$. It shows characteristic absorption bands at 3320 2920, 1830, 1720, 1650, 1610, 1545, 1185, 1120, 885 and 720 cm$^{-1}$ in infra-red absorption spectrum pelleted in potassium bromide. Its nuclear magnetic resonance spectrum (in deutero-chloroform, δ ppm) shows absorptions at 3.2 (2-CH), 4.34 (3-CH), ~2.1 (4-CH$_2$), 5.02 (5-CH), 1.26 (6~15-CH$_2$, 2'~5'-CH$_2$), 0.88 (16-CH$_3$, 6'-CH$_3$), ~1.76 (1'-CH$_2$), 4.72 (2''-CH), 2.76 and 2.98 (3''-CH$_2$), 6.78 (2''-NH), 2.03 (2''-CDCH$_3$), 5.44 and 5.80 (3''-CONH$_2$) (see the above-mentioned formula (I)). These data support the structural formula (II) for tetrahydroesterastin.

(2) 3,5-Di-hydroxy-2-hexylhexadeca-7,10-dienoic 1,3-lactone is obtained as a colorless oily substance of the following properties:

It shows a specific optical rotation $[\alpha]_D^{26} -10°$ (c=1, CHCl$_3$) and a molecular weight of 350 as determined by mass spectrometry. It gives an elemental analysis: C 75.76%, H 10.86%, O 14.00% and is coincident with a molecular formula $C_{22}H_{38}O_3$. It shows characteristic absorption bands at 3500, 3000, 2930, 1820, 1465, 1380, 1122, 1070 and 880 cm$^{-1}$ in infra-red absorption spectrum pelleted in potassium bromide. Its nuclear magnetic resonance absorption spectrum (in deutero-chloroform, δ ppm) shows absorptions at 3.32(2-CH), 4.47(3-CH), ~2.0(4-CH$_2$), 3.79(5-CH), 2.32(6-CH$_2$), 2.80(9-CH$_2$), 5.15~5.72(7,8,10, 11-CH), ~1.3(13~15 CH$_2$, 2'~5'-CH$_2$), 0.89(16-CH$_3$, 6'-CH$_3$), 1.81(1'-CH$_2$) and ~2(OH) (see the formula (I) shown hereinbefore). These data support the above-mentioned formula (III) for this particular compound.

(3) 3,5-Di-hydroxy-2-hexylhexadecanoic 1,3-lactone is obtained as a colorless powdery substance of the following properties:

It shows a melting point of 64.5°–65.5° C. and a specific optical rotation $[\alpha]_D^{26} -15°$(c=1, CHCl$_3$).

It gives an elemental analysis: C 74.22%, H 11.94%, O 13.76% and is coincident with a molecular formula $C_{22}H_{42}O_3$. It shows characteristic absorption bands at 3550, 2900, 1815, 1470, 1390, 1135, 1085, 835 and 720 cm$^{-1}$ in infra-red absorption spectrum pelleted in potassium bromide. Its nuclear magnetic resonance absorption spectrum (in deutero-chloroform, δ ppm) shows absorption at 3.31(2-CH), 4.46(3-CH), 1.7~2.6(4-CH$_2$, 6-CH$_2$, 1'-CH$_2$), 3.76(5-CH), 1.3(7~15-CH$_2$, 2'~5'-CH$_2$), 0.89(16-CH$_3$, 6'-CH$_3$) (see the formula (I) shown hereinbefore). These data support the above-mentioned formula (IV) for this compound.

Esterastin which is used as the starting material for the production of the compounds (II) and (III) of this invention may be prepared by aerobic cultivation of spores or mycelia of an esterastin-producing strain of the genus Streptomyces such as Streptomyces lavendulae MD4-C1 (identified as FERM-P 3723 or ATCC. 31336) in a culture medium comprising known nutrients as the carbon and nitrogen sources until esterastin is produced and accumulated in the culture broth and in the mycelia of the microorganism employed. Generally, the nutrient constituents of the culture medium commonly employed for cultivation of ordinary actinomycetes can be used for this purpose. For instance, glycerin, glucose, lactose, sucrose, starch, maltose and other carbohydrates as well as fat and oil are useful as the carbon source, and peptone, meat extract, cotton seed meal, peanut meal, soybean meal and the like may be useful as the nitrogen source. Glycerin is preferably used as the carbon source, and cotton seed meal and L-asparagine are preferably used as the nitrogen source.

The recovery of esterastin may be conducted in the following way:

After the cultivation, the culture broth is filtered to give the filter cake comprising the mycelia which is then extracted with a water-miscible organic solvent such as methanol, ethanol or acetone. The resulting extract solution is subsequently concentrated to dryness under reduced pressure and the residue is again extracted with an organic solvent such as chloroform, benzene, butyl acetate or ethyl acetate to give an organic solution containing esterastin. This organic solution may be concentrated to dryness to afford a crude powder of esterastin.

The culture broth filtrate obtained as above may be concentrated to dryness under reduced pressure and the solid residue is extracted with an organic solvent such as methanol, ethanol, dimethylsulfoxide, acetone, butyl acetate or chloroform in which esterastin is highly soluble. The organic solution (the extract) of esterastin so obtained is treated with an adsorbent, and this adsorbent containing esterastin is subjected to a desorptive treatment, whereby the recovery of esterastin can be achieved in a high yield. As the adsorbent of this purpose, there may be used an organic adsorbent such as "Amberlite" XAD and other microporous resins, as well as an inorganic adsorbent such as activated carbon, alumina, silica gel and activated magnesium silicate (available as "Florosil").

The purification of esterastin may be conducted by a usual chromatographic method on silica gel. For instance, a crude powder of esterastin which was obtained from the extraction of the mycelia cake with methanol and concentration to dryness of the methanolic extract followed by re-extraction with butyl acetate and second concentration to dryness may be purified by chromatography on silica gel developed with a mixed solvent of chloroform-methanol (80:1) so that esterastin can be eluted out in a yield of 90% or more. In particular, chromatography on silica gel is effective for ultimate purification of esterastin. For instance, when a crude powder of esterastin is subjected to a chromatography on dry silica gel using ethyl acetate as the eluent, a substantially pure esterastin is afforded. This esterastin product can be re-precipitated from chloroform-petroleum ether, for example, to give a pure esterastin as a colorless powder.

According to a second aspect of this invention, there is provided a process for the production of the compound (II), namely tetrahydroesterastin having the formula

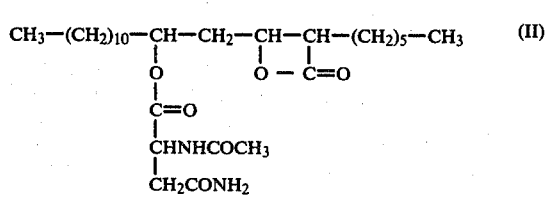

which comprises reducing with hydrogen esterastin having the formula

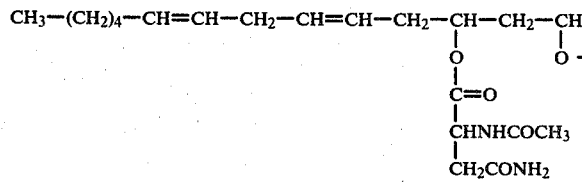

in the presence of a hydrogenation catalyst.

In this process of the second aspect of the invention, the starting esterastin may be dissolved in an organic solvent such as a lower alkanol, for example, methanol or ethanol which is inert to the reaction involved. To this solution is added an amount of a known hydrogenation catalyst such as platinum oxide or palladium metal. The amount of the catalyst may be 2~20% by weight of the starting esterastin. The reduction may carried out in a stream of hydrogen gas or in Parr-apparatus at ambient temperature for a period of time of 2 hours to 12 hours. Usually, it suffices that the catalytic reduction is carried out overnight. After the reaction is completed, the reaction mixture is filtered to remove the catalyst, and the filtrate is concentrated to dryness to afford a crude powder of tetrahydroesterastin.

If necessary, this product can be purified by chromatography on silica gel using a mixed solvent such as ethyl acetate-chloroform as the eluent. Ethyl acetate-chloroform (1:1) is most preferred for the eluent.

According to a third aspect of this invention, there is provided a process for the production of the compound (III), namely 3,5-di-hydroxy-2-hexylhexadeca-7,10-dienoic 1,3-lactone having the formula

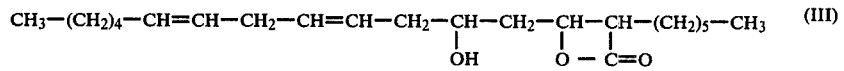

which comprises hydrolyzing esterastin having the formula

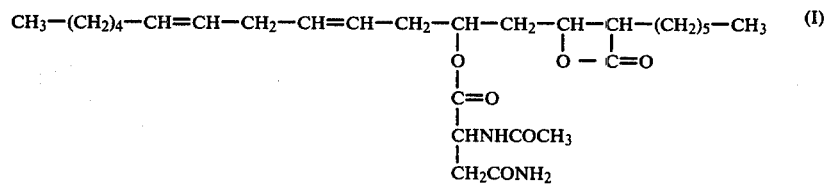

under alkaline conditions.

According to a fourth aspect of this invention, there is provided a process for the production of the compound (IV), namely 3,5-di-hydroxy-2-hexylhexadecanoic 1,3-lactone having the formula

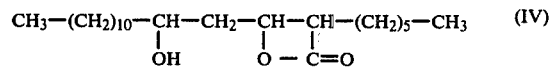

which comprises hydrolyzing tetrahydroesterastin having the formula

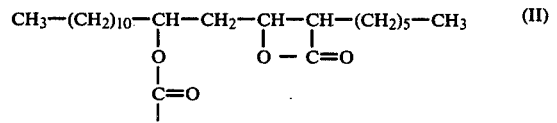

under alkaline conditions.

In these processes of the third and fourth aspects of this invention, the starting esterastin or tetrahydro esterastin may be dissolved in a mixed solvent such as water-dioxane or water-acetone. Water-dioxane (1:1) and water-acetone (1:1) are most preferred as the reaction medium. The solution of esterastin or tetrahydro-esterastin so prepared is admixed with an equivalent or substantially equivalent amount of a week alkali to effect the hydrolysis. The alkali may be an alkali metal hydroxide or carbonate, and 0.01 N aqueous solution of sodium hydroxide or potassium hydroxide is most suitable. The reaction mixture may be stirred at ambient temperature overnight. The reaction mixture may be warmed, if desired. After the hydrolysis reaction is completed, the reaction solution is extracted with n-hexane so that the hydrolysis product (that is, 3,5-di-hydroxy-2-hexylhexadeca-7,10-dienoic 1,3-lactone or 3,5-dihydroxy-2-hexylhexadecanoic 1,3-lactone) is transferred into the n-hexane phase.

The solution (extract) of this hydrolysis product in n-hexane may be purified by chromatography on silica gel. As the eluent for this purpose, n-hexane-chloroform (3:1) is most suitable. In this way, a pure product of the compound (III) or the compound (IV) may be afforded.

According to a fifth aspect of this invention, there is provided a process for the production of the compound (IV), namely 3,5-di-hydroxy-2-hexylhexadecanoic 1,3-lactone, which comprises reducing with hydrogen the compound (III), namely 3,5-di-hydroxy-2-hexylhexadeca-7,10-dienoic 1,3-lactone having the formula

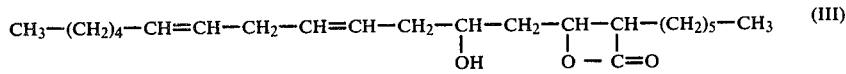

in the presence of a hydrogenation catalyst.

In this process of the fifth aspect of this invention, the reduction of the starting 3,5-di-hydroxy-2-hexylhexadeca-7,10-dienoic 1,3-lactone with hydrogen is carried out in the presence of a known hydrogenation catalyst such as platinium oxide or palladium metal in the same way as in the process of the aforesaid second aspect of this invention. Thus, the starting compound (III) is dissolved in an organic solvent such as a lower alkanol, and to this solution is added an amount of a hydrogenation catalyst. This mixture is reduced under a stream of hydrogen or in a Parr-apparatus for a period of time of 2 hours to 1 hours to give 3,5-di-hydroxy-2-hexylhexadecanoic 1,3-lactone as the hydrogenation product. If the starting 3,5-di-hydroxy-2-hexylhexadeca-7,10-dienoic 1,3-lactone employed is pure, purification of the hydrogenation product so obtained is not necessary.

The esterase-inhibiting activity of the new compounds of this invention can be determined according to a modification of the method of Yasunori Kobayashi described in a Japanese literature "Seikagaku" Vol. 36, page 335(1964). Thus, a commercially available, crude lipase preparation obtained from pig pancreas is dissolved to a concentration of 0.5% (by weight) in a 0.05M phosphate buffered solution (pH 7.0) containing 0.2% "Triton X-100" (a trade name of an emulsifier consisting of a polyethyleneglycol alkylphenylether, a product of Rohm & Haas Co., U.S.A.). This lipase solution (0.03 ml), 2.92 ml of 0.05 M phosphate buffered solution (pH 7.0) and 0.025 ml of a solution containing a sample of the new compound to be assayed are mixed together, and the resulting mixture (2.975 ml) is warmed at 20° C. for 3 minutes and then admixed with 0.025 ml of a solution containing 10 mg/ml of p-nitrophenyl acetate in methanol to start the reaction of p-nitrophenyl acetate with lipase. After the enzymatic reaction is effected at 20° C. for 30 minutes, absorbance (a) at 400 nm of the resulting reaction solution is measured. On the other hand, absorbance (b) at 400 nm of a control reaction solution obtained from the blank test using the 0.05M phosphate buffered solution not containing the new compound to be assayed is measured in the same way as above. Degree (%) of inhibition to esterase is calculated according to the following equation:

$$\text{Inhibition}(\%) = \frac{(b - a)}{b} \times 100$$

In accordance with this assay method, the pure product of tetrahydroesterastin had a potency such that its $ID_{50}$, namely the dose of giving 50% inhibition to esterase amounted to 0.0033 µg/ml. 3,5-Di-hydroxy-2-hexylhexadeca-7,10-dienoic 1,3-lactone and 3,5-di-hydroxy-2-hexylhexadecanoic 1,3-lactone had a potency such that its $ID_{50}$ to esterase amounted to 0.007 µg/ml and 0.009 µg/ml, respectively. For comparison, the colorless powder of the parent esterastin had a potency such that its $ID_{50}$ to esterase amounted to 0.0002 µg/ml.

As esterastin is a fairly unstable substance, it is necessary to dissolve esterastin in a suitable organic solvent such as chloroform and to keep the solution at a low temperature in order to store esterastin without degradation. In contrast, the new compound, tetrahydroesterastin is fairly stable so that it can be stored in the form of a powder as such for a long time of 1 year or more without lowering its activity.

Furthermore, the new compounds of this invention all have advantageously a remarkably higher activity of inhibiting cholesterol esterase than the parent esterastin. Thus, when the effect of the new compounds of this invention to inhibit cholesterol esterase is estimated by using cholesterol acetate as the substrate and a cholesterol esterase (available from Boehringer Mannheim Co., U.S.A) as the reactant enzyme and determining the quantity of the cholesterol liberated from the reaction of the substrate and the enzyme at 37° C. for 3 minutes, it has been found that tetrahydroesterastin is about 3-fold higher than the parent esterastin in its cholesterol esterase-inhibiting activity, and that 3,5-di-hydroxy-2-hexylhexadeca-7,10-dienoic 1,3-lactone is about 20 times higher than the parent esterastin and is about 7 times higher than tetrahydroesterastin in its cholesterol esterase-inhibiting activity.

The new compounds (V) of this invention all are of a very low toxicity as shown by the fact that no toxicity was observed at all when a dose of 250 mg/kg (by intraperitoneal injection) was given to mice for estimation of acute toxicity. It is known that paradoxon and di-isopropyl fluorophosphate inhibit the esterase of pig pancrease, but these known compounds are highly toxic. The new compounds of the invention are not toxic and strongly inhibit the activity of the pig pancreas esterase to the extent that the compound (II) of this invention at a low level of $6.4 \times 10^{-9}$ M and the compounds (III) and (IV) of this invention at a low level of $2 \times 10^{-8}$ M and $2.5 \times 10^{-8}$ M, respectively, gives 50% inhibition of the esterase when estimated using p-nitrophenyl acetate as the substrate.

Because of the esterase-inhibiting activity, the new compounds (V) of this invention, similarly to the parent esterastin, may be used as a drug for chemotherapeutically treating many diseases such as contact allergic dermatitis, systemic lupus erythematosus, autoimmune hemolytic anemia, periarteritis nodosa, myasthenia gravis, arthritis, rheumatism and multiple sclerosis, and may be used as an agent to suppress the rejection syndrome in the surgical operations of transplantation of internal organs such as the heart and kidneys. In addition, because of the cholestrol esterase-inhibiting activity, the new compounds of this invention may also be used as a drug for chemotherapeutically treating thrombosis and arteriosclerosis.

According to this invention, therefore, there is provided a pharmaceutical composition for suppressing or reducing the immune response in animals including man, which comprises an effective amount of at least one of the new compounds of the formula (V) of this invention as the active ingredient, in association with a pharmaceutically acceptable carrier for the active ingredient.

According to this invention, there is further provided the method for chemotherapeutically treating immune diseases and disorders which comprises administering to a living animal a pharmaceutical composition to suppress or reduce the immune response comprising an effective amount of a suppressing or reducing compound of the aforesaid formula (V), in combination with a pharmaceutically acceptable non-toxic carrier.

The pharmaceutical composition of this invention may be formulated as conventional orally administerable forms such as tablets, capsules, powders, solutions and suspensions, either by admixing an amount of a new compound of this invention with a conventional pharmaceutically acceptable solid carrier such as starch, sucrose, talc or calcium carbonate or by dissolving or suspending an amount of a new compound of this invention in a pharmaceutically acceptable liquid carrier such as ethanol or water. The proportion of the active compound of this invention to the solid or liquid carrier may be chosen appropriately depending on the form of the orally administerable formulation prepared and usually may be in a ratio of from 1:1 to 1:100 by weight.

The pharmaceutical composition of this invention may also be formulated into injectable solutions or suspensions by dissolving or suspending the active compound at a suitable level of from 0.1% to 10% by weight into a physiological saline solution or other conventional pharmaceutically acceptable liquid vehicle such as Ringer's solution, with or without aid of a suitable dispersion agent. The injectable solution or suspension so prepared may be given, eg. by intravenous injection, intramuscular injection or intraperitoneal injection.

It will be appreciated that the actual preferred dosage of the active compound of this invention used will vary according to the particular composition formulated for administration, the mode of administration and the particular disease to be treated. Many factors that modify the action of the drug of this invention will be taken into account by the skilled in the art, for example, age, body weight, sex, diet, time of administration, route of administration, rate of excretion, drug combinations, reaction sensitivities and severity of the disease. Generally, about 0.5 mg/kg to about 100 mg/kg of the active compound is given a day to an adult person. Optimal dosages for a given set of conditions of a patient can be ascertained by the skilled in the art using conventional dosage determination tests in view of the above guidelines and in view of the past experiences as obtained when determining suitable dosages of the previously known immunosuppressive drugs such as Immuran (6-mercaptopurine).

It is believed that using the preceding description and without further elaboration, one skilled in the art can utilize the concept of this invention to its full extent. The following preferred specific embodiments are, therefore, to be construed as merely illustrative of this invention.

This invention is now illustrated with reference to the following Examples.

EXAMPLE 1

Preparation of esterastin (a) A culture medium (300 l) comprising 1.5% glycerin, 1.5% cotton seed meal, 0.3% sodium chloride, 0.2% L-asparagine and 0.005% antifoaming agent (polyoxyalkylene commercially available under a tradename "Adecanol," a product of Asahi Denka Co., Japan) was charged in a stainless steel tank of 570 l capacity and then sterilized by heating at 120° C. for 20 minutes. To this sterilized culture medium was inoculated 30 l of a seed culture which was obtained by incubating Streptomyces MD4-C1 strain (FERM-P 3723 or ATCC. No. 31336) for 2 days at 27° C. under aeration and agitation. The inoculated culture medium was incubated at 27° C. for 48 hours at a rate of aeration of 300 l/minute and at an agitator speed of 200 r.p.m. The fermentation broth so obtained was filtered to give 34.2 kg of the filter cake containing the mycelia. This filter cake was extracted twice each with 100 l of ethanol, and the combined ethanolic extracts were concentrated to a volume of 6 l under reduced pressure. The concentrated solution was extracted twice each with 6 l of butyl acetate. The extracts in butyl acetate were combined together and concentrated under reduced pressure to give 128.2 g of a crude powder of esterastin which had a potency corresponding to an $ID_{50}$ value of 0.08 mcg/ml.

(b) The crude powder of esterastin obtained as above was purified in the following procedure. This crude powder (128.2 g) was dissolved in 500 ml of chloroform and the resultant solution was passed through a column of 1.5 kg of silica gel (Wako-gel C-100) for adsorption of esterastin. The silica gel column was washed with 10 l of chloroform and then with 10 l of chloroform-methanol (100:1 by volume), followed by elution with chloroform-methanol (80:1 by volume). The active fractions (2500 ml) of the eluate were combined together and concentrated to dryness under reduced pressure to afford 4.83 g of a brown colored crude powder which had a potency corresponding to an $ID_{50}$ value of 0.002 mcg/ml. This crude powder was taken up into 20 ml of methanol and the solution obtained was passed through a column of 2 l of Sephadex LH-20 which had been swollen with methanol. This column was then eluted with 4 l of methanol. The active fractions of the eluate were combined together and concentrated to dryness under reduced pressure to yield 656 mg of a lightly yellow colored powder ($ID_{50}$=0.0004 mcg/ml). This powder was taken up into 5 ml of ethyl acetate and the solution obtained was passed through a column of 250 g of silica gel (Wako-gel C-300) for adsorption of esterastin. This silica gel column was then developed with ethyl acetate, and the active fractions of the eluate were combined together (1000 ml) and concentrated to dryness under reduced pressure, affording 351 mg of a colorless powder of esterastin which had a potency corresponding to an $ID_{50}$ value (to esterase) of 0.0002 mcg/ml.

EXAMPLE 2

Production of tetrahydroesterastin

Esterastin (95 mg) was taken up into 10 ml of methanol, and this methanolic solution of esterastin was admixed with 20 mg of platinum oxide as the hydrogenation catalyst. The mixture was subjected to hydrogenation with hydrogen gas at 20 lbs. per square inch at ambient temperature for 2 hours. After the reduction was completed, the reaction mixture was filtered to remove the platinum oxide. The filtrate (the reaction solution) was concentrated to dryness to yield 96 mg of a colorless powder of tetrahydroesterastin which gave a single spot in a silica gel thin layer chromatography.

EXAMPLE 3

Production of tetrahydroesterastin

A solution of 10 mg of esterastin in 0.5 ml of 99% aqueous methanol was hydrogenated with hydrogen gas at 20 lbs. per square inch in the presence of 2 mg of the platinum oxide catalyst at ambient temperature for 2 hours. The reaction mixture was filtered to remove the platinum oxide, and the filtrate was concentrated to dryness to give 9.7 mg of a colorless powder. This powder was chromatographed in a column of silica gel using a mixed solvent of ethyl acetate-chloroform (1:1) as the eluent. A colorless powder of tetrahydroesterastin (5.9 mg) was obtained, which gave a single spot on a silica gel thin layer chromatogram.

EXAMPLE 4

Production of 3,5-di-hydroxy-2-hexylhexadeca-7,10-dienoic 1,3-lactone

Esterastin (275 mg) was dissolved in 55 ml of a solution containing 0.01 N sodium hydroxide dissolved in a mixture of water-dioxane (1:1 by volume), and the resulting solution was stirred overnight at ambient temperature to effect the hydrolysis of esterastin. The reaction mixture was then extracted three times each with 55 ml portions of n-hexane. The n-hexane extracts so obtained were combined together and concentrated, and the resultant oily residue (150 mg) comprising the n-hexane soluble matter was chromatographed in a column of silica gel (1.0×15 cm) using a mixed solvent of n-hexane-chloroform (3:1) as the eluent. The eluate was collected in 5 ml-fractions, and the fractions Nos. 56~65 were combined together and concentrated to give 140 mg of a colorless oil essentially consisting of 3,5-di-hydroxy-2-hexylhexadeca-7,10-dienoic 1,3-lactone.

This product gave a single spot at $R_f 0.73$ on a silica gel thin layer chromatogram developed with a solvent system of n-hexane-chloroform-ethyl acetate (5:5:1).

EXAMPLE 5

Production of 3,5-di-hydroxy-2-hexylhexadecanoic 1,3-lactone

Tetrahydroestrastin (212 mg) was suspended in 46 ml of a solution containing 0.01 N sodium hydroxide dissolved in a mixture of water-dioxane (1:1), and the resulting admixture was stirred at ambient temperature overnight to effect the hydrolysis of tetrahydroesterastin. The reaction mixture was then extracted three times each with 50 ml portions of n-hexane. The n-hexane extracts so obtained were combined together and concentrated to dryness. The resulting solid residue comprising the n-hexane soluble matter (156 mg) was chromatographed in a column of silica gel (1.0×15 cm) using a mixed solvent of n-hexane-chloroform (3:1) as the eluent. The eluate was collected in 2 ml-fractions, and the fraction Nos. 24~41 were combined together and concentrated to dryness to give 106 mg of a colorless powder of 3,5-di-hydroxy-2-hexylhexadecanoic 1,3-lactone.

This product gave a single spot at $R_f 0.74$ on a silica gel thin layer chromatogram developed with a solvent system of n-hexane-chloroform-ethyl acetate (5:5:1).

EXAMPLE 6

Production of 3,5-di-hydroxy-2-hexylhexadecanoic 1,3-lactone 3,5-Di-hydroxy-2-hexylhexadeca-7,10-dienoic 1,3-lactone (140 mg) which was obtained in Example 4 was dissolved in 10 ml of methanol, and the resulting methanolic solution was admixed with 40 mg of platinum oxide as the hydrogenation catalyst. The admixture so obtained was subjected to a catalytic hydrogenation in a Parr-apparatus by reacting with hydrogen at 20 lbs. per square inch at ambient temperature for 2 hours. The reaction mixture was filtered to remove the platinum oxide catalyst, and the filtrate was concentrated to dryness to give 141 mg of a colorless powder of 3,5-di-hydroxy-2-hexylhexadecanoic 1,3-lactone.

This product gave a single spot at $R_f 0.74$ on a silica gel thin layer chromatogram developed with a solvent system of n-hexane-chloroform-ethyl acetate (5:5:1), and a nuclear magnetic resonance spectrum of this product showed complete disappearance of the double bonds of the starting compound.

We claim:

1. The compound having the formula

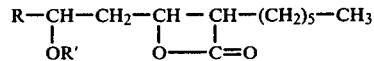

wherein R denotes a group of the formula $CH_3-(CH_2)_4-CH=CH-CH_2-CH=CH-CH_2-$ or a group of the formula $CH_3-(CH_2)_{10}-$ and R' denotes a hydrogen atom or a group of the formula

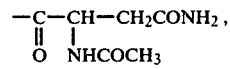

provided that when R' is the group

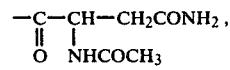

R is the group $CH_3-(CH_2)_{10}-$.

2. The compound according to claim 1 and having the formula

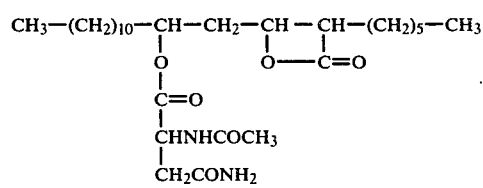

which is designated tetrahydroesterastin.

3. The compound according to claim 1 and having the formula

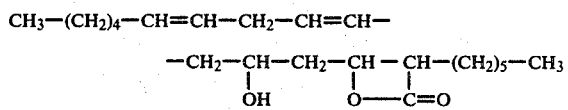
CH₃—(CH₂)₄—CH=CH—CH₂—CH=CH—
—CH₂—CH—CH₂—CH — CH—(CH₂)₅—CH₃
           |            |      |
           OH           O——C=O which is named 3,5-di-hydroxy-2-hexylhexadeca-7,10-dienoic 1,3-lactone.

4. The compound according to claim 1 and having the formula $$CH_3-(CH_2)_{10}-\underset{\underset{OH}{|}}{CH}-CH_2-\underset{\underset{O\ -\ C=O}{|\quad\quad|}}{CH-CH}-(CH_2)_5-CH_3$$

which is named 3,5-di-hydroxy-2-hexylhexadecanoic 1,3-lactone.

* * * * *